(12) United States Patent
Qiu et al.

(10) Patent No.: US 10,596,077 B2
(45) Date of Patent: Mar. 24, 2020

(54) METHOD FOR PREPARING A DENTAL COMPOSITE RESIN MATERIAL AND ARTICLES PREPARED THEREFROM

(71) Applicant: Liaoning Upcera Co., Ltd., Benxi, Liaoning (CN)

(72) Inventors: Yuexiu Qiu, Benxi (CN); Hongjuan Wang, Benxi (CN); Dapeng Yuan, Benxi (CN); Bin Sun, Benxi (CN); Feng Shi, Benxi (CN)

(73) Assignee: LIAONING UPCERA CO., LTD., Benxi, Liaoning (CN)

( * ) Notice: Subject to any disclaimer, the term of this patent is extended or adjusted under 35 U.S.C. 154(b) by 211 days.

(21) Appl. No.: 15/569,543

(22) PCT Filed: Apr. 18, 2017

(86) PCT No.: PCT/CN2017/080865
§ 371 (c)(1),
(2) Date: Oct. 26, 2017

(87) PCT Pub. No.: WO2017/219742
PCT Pub. Date: Dec. 28, 2017

(65) Prior Publication Data
US 2018/0221250 A1     Aug. 9, 2018

(30) Foreign Application Priority Data
Jun. 23, 2016   (CN) .......................... 2016 1 0463669

(51) Int. Cl.
| | | |
|---|---|---|
| A61K 6/083 | (2006.01) | |
| C08F 220/32 | (2006.01) | |
| A61L 27/50 | (2006.01) | |
| C08F 2/44 | (2006.01) | |
| A61K 6/00 | (2020.01) | |
| C08K 3/22 | (2006.01) | |
| C08K 3/40 | (2006.01) | |
| C08K 7/10 | (2006.01) | |
| C08K 7/14 | (2006.01) | |

(52) U.S. Cl.
CPC ............ *A61K 6/083* (2013.01); *A61K 6/0088* (2013.01); *A61K 6/0091* (2013.01); *A61K 6/0094* (2013.01); *A61K 6/0097* (2013.01); *A61L 27/50* (2013.01); *C08F 2/44* (2013.01); *C08F 220/32* (2013.01); *C08K 3/22* (2013.01); *C08K 3/40* (2013.01); *C08K 7/10* (2013.01); *C08K 7/14* (2013.01); *C08K 2003/2265* (2013.01)

(58) Field of Classification Search
None
See application file for complete search history.

(56) References Cited

U.S. PATENT DOCUMENTS

| | | | | |
|---|---|---|---|---|
| 6,362,250 | B1 * | 3/2002 | Karmaker ............ | A61K 6/0073 433/212.1 |
| 7,579,408 | B2 * | 8/2009 | Walton ................... | C08L 23/06 525/191 |
| 2001/0001510 | A1 * | 5/2001 | Rheinberger ......... | A61C 13/0003 264/17 |
| 2001/0036617 | A1 * | 11/2001 | Karmaker ............ | A61C 13/0003 433/173 |
| 2008/0300340 | A1 * | 12/2008 | Gross ..................... | A61K 6/083 523/120 |
| 2009/0258965 | A1 | 10/2009 | Lassila et al. | |
| 2013/0203884 | A1 * | 8/2013 | Blomker ................ | A61K 6/083 522/48 |
| 2014/0303296 | A1 * | 10/2014 | Inazawa .................. | C08L 27/18 524/127 |
| 2018/0221250 | A1 * | 8/2018 | Qiu ........................ | A61K 6/0088 |

FOREIGN PATENT DOCUMENTS

| | | |
|---|---|---|
| CN | 1911204 | 2/2007 |
| CN | 101244013 | 8/2008 |
| CN | 101244013 A | 8/2008 |
| CN | 101288627 | 10/2008 |
| CN | 101288627 A | 10/2008 |
| CN | 101489518 | 7/2009 |
| CN | 101518499 | 9/2009 |
| CN | 101617962 | 1/2010 |
| CN | 101617962 A | 1/2010 |
| CN | 103211711 | 7/2013 |
| CN | 103211711 A * | 7/2013 |
| CN | 103356392 | 10/2013 |
| CN | 103356392 A | 10/2013 |
| JP | 56-118009 | 9/1981 |

(Continued)

OTHER PUBLICATIONS

International Search Report by the International Searching Authority for the International Application No. PCT/CN2017/080865, dated Jun. 22, 2017 (4 pages) with English translation (2 pages). (6 pages total).

(Continued)

*Primary Examiner* — Peter A Salamon
(74) *Attorney, Agent, or Firm* — Daniel F. Nesbitt; Hasse & Nesbitt LLC

(57) ABSTRACT

The examples of the present application disclose a method for preparing a dental composite resin material and articles prepared therefrom, wherein the method comprises: (1) weighing in each of raw materials, including ethylenically unsaturated monomer, reinforcing fiber, filler, initiator, polymerization inhibitor and colorant; (2) mixing the weighed raw materials except reinforcing fiber, obtaining a composite resin monomer precursor; (3) impregnating the weighed reinforcing fiber into the composite resin monomer precursor for 1-5 hours, preferably 2-3 hours, at an impregnation negative pressure of less than or equal to 0.1 MPa, obtaining a composite resin monomer precursor-immersed reinforcing fiber; and (4) subjecting the composite resin monomer precursor-immersed reinforcing fiber to a solidification treatment, obtaining the dental composite resin material. The flexural strength of the dental composite resin material provided by the present application is above 600 MPa, and the light transmittance can be up to above 40%.

18 Claims, No Drawings

(56) References Cited

FOREIGN PATENT DOCUMENTS

| JP | H07291819 A | 11/1995 |
|---|---|---|
| JP | 2003104822 A | 4/2003 |
| JP | 2009541568 | 11/2009 |
| JP | 2015067543 A | 4/2015 |
| WO | 2008000917 | 1/2008 |

OTHER PUBLICATIONS

First Office Action dated May 18, 2018 in corresponding Korean Application No. 10-2017-7033360 (8 pages) with English machine translation from KIPO (9 pages).
Zhang, "The Foundation and Clinic of Oral Prosthesis", Feb. 9, 2004, Shanghai Scientific and Technological Literature Press, p. 205-210 (6 pages) with English translation (8 pages).
First Office Action dated Apr. 3, 2019 in corresponding Chinese Application No. 201610463669.3 (8 pages) with English machine translation (8 pages).
Karacaer, et al., "Dynamic mechanical properties of dental base material reinforced with glass fiber", Aug. 22, 2002, Journal of Applied Polymer Science, vol. 85 No. 8, p. 1683-97 (15 pages).
Office Action dated May 18, 2018 in corresponding Korean Application No. 10-2017-7033360 (8 pages) with English machine translation from KIPO (9 pages).
Final Office Action dated Jan. 15, 2019 in corresponding Japanese Application No. 2017-557191 (2 pages) with English machine translation from JPO (4 pages).
Supplemental European Search Report dated Dec. 20, 2018 in corresponding European Application No. 17 800 995.7 (5 pages).

\* cited by examiner

METHOD FOR PREPARING A DENTAL COMPOSITE RESIN MATERIAL AND ARTICLES PREPARED THEREFROM

CROSS-REFERENCE TO RELATED APPLICATIONS

This application is a U.S. National Stage of International Application No. PCT/CN2017/080865, filed Apr. 18, 2017, the content of which is incorporated herein by reference in its entirety.

TECHNICAL FIELD

The present application relates to the field of dental restorations, and particularly relates to a method for preparing a dental composite resin material and articles prepared therefrom.

BACKGROUND ART

The Computer Aided Design and Computer Aided Manufacture (CAD/CAM) technologies was firstly introduced into the design and manufacture of oral fixed restoration in the early 1970s by Professor Francois Duret of France, These technologies brought a great technological revolution in the field of dental restoration. Therein, CAD means using computer as the major technological to create and apply various digital and graphic information for article designation: and CAM means an automatically manufacture technology for article machining via a computer-controlled machining equipment, such as CNC (Computer Numerical Control) milling machine. At present, the CAD/CAM systems can successfully manufacture fixed restorations, such as inlay, veneer, crown, fixed bridge and so on. However, patients have to go to the hospital at least 2-3 times to finish the completely therapeutic process. Such frequent and complex subsequent visits put patients to great inconvenience. With the development of computer technology, a new technology, chair-side digital restoration technology (chair-side CAD/CAM), emerges which can treat patients rapidly.

In Chair-side CAD/CAM system, a Computer Aided Design and Computer Aided Manufacture device is placed at the side of dental chair. After tooth preparation and the like, the tooth model of patient can be obtained through digital technology, and then the data can be analyzed by computer, and a dental prosthesis (restoration) can be designed and manufactured immediately. It will take patient around 30 minutes to finish the completely treatment, without complex subsequent visits. With chair-side CAD/CAM technology, the temporary restoration can be prohibited, the manufacture of restoration can be completed in one-step, thus, saving time for patient, and significantly improving the quality of the restoration. Through digital model scanning, restoration designing and manufacturing the dental restoration can achieve better precision and accuracy, and thus improving the treatment success rate. The problems caused by conventional PFM (Porcelain Fused to Metal) denture and removable denture, such as gingiva discoloration and marginal unfitness, can be greatly reduced, and the patient's satisfaction for the treatment can be improved significantly.

The development of the chair-side CAD/CAM also drives the development of the dental material. At present, there are three kinds of dental materials been developed for chair-side CAD/CAM: machinable ceramic, composite and metal. The machinable ceramic includes glass ceramic, glass-infiltrated hybrid ceramic, alumina, zirconia, and the like. The composite material includes resin composite, resin-infiltrated porous ceramic hybrid material, poly(ether-ether-ketone) (PEEK) material, and the like. The metal is dental titanium and the like.

Among the three materials mentioned above, the resin composite material is an ideal candidate for the dental chair-side CAD/CAM owning to its good toughness, machinability, abrasive resistance, X-ray resistance and easily polishing. In addition, the aesthetic effect thereof is similar to natural tooth. However, the strength of CAD/CAM resin composite is too low with the maximum bending strength of around 240 MPa, which can be applied for non-weight bearing restorations, such as the inlay, onlay, veneer, single crown. CAD/CAM resin composite can not be used for bearing dental restorations, such as bridge, molar tooth and the like.

SUMMARY OF THE INVENTION

The examples of the present application disclose a method for preparing a dental composite resin material and articles prepared therefrom, in order to address the low strength problem of the CAD/CAM composite resin material. The technical solutions are as follows.

The present application firstly provides a method for preparing a dental composite resin material, comprising:

(1) weighing in each of raw materials, including ethylenically unsaturated monomer, reinforcing fiber, filler, initiator, polymerization inhibitor and colorant; wherein the ratio of the total weight of the reinforcing fiber and filler to the weight of the ethylenically unsaturated monomer is 90:10-10:90, preferably 85:15-65:35; the initiator is 0.05-1%, preferably 0.1-0.3% by weight relative to the weight of the ethylenically unsaturated monomer; the polymerization inhibitor is 0.05-1%, preferably 0.1-0.3% by weight relative to the weight of the ethylenically unsaturated monomer; the colorant is 0.001-0.2%, preferably 0.005-0.1% by weight relative to the total weight of the ethylenically unsaturated monomer, the reinforcing fiber and the filler; and the weight ratio of the filler to the reinforcing fiber is 10:90-55:45;

(2) mixing the weighed raw materials except reinforcing fiber, obtaining a composite resin monomer precursor;

(3) impregnating the weighed reinforcing fiber into the composite resin monomer precursor for 1-5 hours, preferably 2-3 hours, at an impregnation negative pressure of less than or equal to 0.1 MPa, obtaining a composite resin monomer precursor-immersed reinforcing fiber; and (4) subjecting the composite resin monomer precursor-immersed reinforcing fiber to a solidification treatment, obtaining the dental composite resin material, wherein the solidification temperature is 100-200° C., preferably 120-160° C., the solidification time is 0.5-3 hours, preferably 1.5-2 hours, and the solidification pressure is 10-200 MPa, preferably 10-100 MPa, and more preferably 20-60 MPa.

In one particular embodiment of the present application, the raw materials further include accelerant, which is 0.05-1%, preferably 0.1-0.3% by weight relative to the weight of the ethylenically unsaturated monomer, and preferably, the amine accelerant is N,N-dihydroxyethyl-4-methylaniline.

In one particular embodiment of the present application, the raw materials further include at least one of fluorescer, indicator, viscosity modifier, wetting agent, antioxidant, stabilizer, and diluent.

In one particular embodiment of the present application, the ethylenically unsaturated monomer includes one of (methyl)acrylate, hydroxyl functionalized (methyl)acrylate and epoxy or a combination thereof, and preferably includes one of bisphenol A-glycidyl methacrylate, ethoxylated bisphenol A dimethacrylate, urethane dimethacrylate, triethylene-glycol dimethacrylate, hydroxyethyl methacrylate, poly (ethylene glycol) dimethacrylate and bisphenol A epoxy resin or a combination thereof.

In one particular embodiment of the present application, the reinforcing fiber includes one of carbon fiber, glass fiber, quartz fiber, siliceous fiber, ceramic fiber and polymer fiber or a combination thereof. The reinforcing fiber is fiber bundle, fiber fabric or fiber block; the diameter of a single fiber of the reinforcing fiber is in the range of 0.1-25 µm, preferably 0.5-10 µm; and the refractive index of the reinforcing fiber is in the range of 1.40-1.70, preferably 1.45-1.60.

In one particular embodiment of the present application, the filler includes type I filler and type II filler. The type I filler has particle size in the range of 0.01-10 µm, and selected from inorganic fillers, and/or pre-polymerized organic fillers which are insoluble in the composite resin monomer precursor. The type I filler preferably includes at least one of quartz, barium glass, lanthanum glass, borosilicate glass, silicon oxide-zirconium oxide composite powder, silicon oxide-ytterbium oxide composite powder, polycarbonate filled with or not filled with inorganic material, polyepoxide powder and polymerized methacrylic resin. The refractive index of the type I filler is in the range of 1.48-1.60, preferably 1.50-1.58. The type II filler has a particle size range of 10-100 nm; the type II filler preferably includes at least one of silicon oxide nano-powder and zirconium oxide nano-powder; and the weight ratio of the type I filler to the type II filler is 3:1-1:1.

In one particular embodiment of the present application, the filler is subjected to surface modification before it is mixed with other raw materials, and the methods for the surface modification includes coupling agent modification, plasma surface treatment modification, or chemical grafting modification.

In one particular embodiment of the present application, the colorant includes one of a red colorant, a yellow colorant and a black colorant, or a combination thereof. The red colorant is preferably iron oxide red; the yellow colorant is selected from one of iron oxide yellow, bismuth yellow, vanadium-zirconium yellow and cerium-praseodymium yellow, or a combination thereof; and the black colorant is preferably iron oxide black.

In one particular embodiment of the present application, the initiator is selected from one of dicumyl peroxide, t-butyl peroxide, benzoyl peroxide, t-butyl peroxyacetate and t-butyl peroxybenzoate, or a combination thereof; and the polymerization inhibitor is 2,6-di-t-butyl-p-cresol.

In one particular embodiment of the present application, the reinforcing fiber is subjected to a pre-treatment before impregnating, and the pre-treatment comprises cleaning and surface modification;

Wherein the methods for cleaning include heat treatment, solvent impregnation method or acid/base corrosion method; and the methods for the surface modification include coupling agent modification, plasma surface modification or chemical grafting modification.

The present application also provides a dental composite resin material prepared with the above methods.

The dental composite resin material prepared with the method provided by the present application has following advantageous effects:

(1) the dental composite resin material provided by the present application has extremely high mechanical strength, and the flexural strength via experimental determination is up to above 600 MPa, so that the dental composite resin material can be used for manufacturing a dental restoration for the weight-bearing parts, such as dental bridge, weight-bearing dental crown, complete denture, the scaffold for implant restoration and the like;
(2) the dental composite resin material provided by the present application has no detectable ethylenically unsaturated monomer residue (no cell toxicity), and thus has very good biosecurity; and
(3) the dental composite resin material provided by the present application has a transparency similar to that of a natural tooth, and the light transmittance can be up to above 40%, preferably up to above 55%, such that the dental composite resin material can be used for manufacturing complete dentures.

DETAILED DESCRIPTION OF THE INVENTION

The present application provides a method for preparing a dental composite resin material, comprising the following steps.

Step (1) Weighing in each of raw materials, including ethylenically unsaturated monomer, reinforcing fiber, filler, initiator, polymerization inhibitor and colorant; wherein the ratio of the total weight of the reinforcing fiber and the filler to the weight of ethylenically unsaturated monomer is 90:10-10:90, preferably 85:15-65:35; the initiator is 0.05-1%, preferably 0.1-0.3% by weight relative to the weight of the ethylenically unsaturated monomer; the polymerization inhibitor is 0.05-1%, preferably 0.1-0.3% by weight relative to the weight of ethylenically unsaturated monomer; the colorant is 0.001-0.2%, preferably 0.005-0.1% by weight relative to the total weight of the ethylenically unsaturated monomer; the reinforcing fiber and the filler; and the weight ratio of the filler to the reinforcing fiber is 10:90-55:45.

In a particular embodiment of the present application, the ethylenically unsaturated monomer includes one of (methyl) acrylate, hydroxyl functionalized (methyl)acrylate and epoxy, or a combination thereof, and preferably includes one of bisphenol A-glycidyl methacrylate (Bis-GMA), ethoxylated bisphenol A dimethacrylate (Bis-EMA), urethane dimethacrylate (UDMA), triethylene-glycol dimethacrylate (TEGDMA), hydroxyethyl methacrylate (HEMA), poly (ethylene glycol) dimethacrylate (PEGDMA) and bisphenol A epoxy resin (epoxy resin E-44), or a combination thereof.

In a particular embodiment of the present application, the reinforcing fiber includes one of carbon fiber, glass fiber, quartz fiber, siliceous fiber, ceramic fiber and polymer fiber, or a combination thereof. The reinforcing fiber can be fiber bundle, fiber fabric or fiber block. The diameter of a single fiber of the reinforcing fiber is in the range of 0.1-25 µm, preferably 0.5-10 µm; and the refractive index of the reinforcing fiber is in the range of 1.40-1.70, preferably 1.45-1.60.

In a particular embodiment of the present application, the filler includes type I filler and type II filler. The type I filler is a filler with a particle size in the range of 0.01-10 µm, preferably 0.01-5 µm, and more preferably 0.01-1 µm. The type I filler can be inorganic fillers, or pre-polymerized organic fillers which are insoluble in the composite resin monomer precursor, or a combination of both. The type I filler includes but not limit to at least one of quartz, barium glass, lanthanum glass, borosilicate glass, silicon oxide-zirconium oxide composite powder, silicon oxide-ytterbium oxide composite powder, polycarbonate filled with or not filled with inorganic material, polyepoxide powder and polymerized methacrylic resin.

The refractive index of the type I filler is in the range of 1.48-1.60, preferably 1.50-1.58. The type II filler is a filler with particle size in the range of 10-100 nm, preferably 10-70 nm, and more preferably 15-50 nm. The type II filler preferably includes at least one of silicon oxide nanopowder and zirconium oxide nanopowder, and the weight ratio of the type I filler to the type II filler is 3:1-1:1.

The ethylenically unsaturated monomer, reinforcing fiber and filler used in the present application have a refractive index close to each other, so that the appearance of the dental composite resin material prepared by the present application can be much closer to natural tooth. The combination of the reinforcing fiber and resin material can significantly increase the strength of the resin material, allowing it to satisfy the requirement for producing weight-bearing restorations, such as dental bridge, molar teeth and the like. In addition, the inventors surprisingly found that the addition of the filler could increase the polishability and abrasive resistance of the material. Further, the inventors surprisingly found the mixed use of the type I filler and type II filler can make the dental composite resin material provided by the present application have translucence and opalescence effects similar to those of natural tooth.

In a particular embodiment of the present application, the colorant includes one of red colorant, yellow colorant and black colorant, or a combination thereof. The red colorant preferably is iron oxide red, the yellow colorant is selected from one of iron oxide yellow, bismuth yellow, vanadium-zirconium yellow and cerium-praseodymium yellow, or a combination thereof, and the black colorant preferably is iron oxide black. It can be understood that the amounts of various colorants and the ratio there between can be adjusted according to the actual requirement in order to allow the material color to be close to natural tooth color.

In a particular embodiment of the present application, the initiator can be selected from one of dicumyl peroxide, t-butyl peroxide, benzoyl peroxide, t-butyl peroxyacetate and t-butyl peroxybenzoate, or a combination thereof. The polymerization inhibitor can be 2,6-di-t-butyl-p-cresol, of course, other initiators and polymerization inhibitors can also be used. Preferably, the raw materials can further include accelerant, the accelerant is 0.05-1%, preferably 0.1-0.3% by weight relative to the weight of ethylenically unsaturated monomer; and the amine accelerant can be N,N-dihydroxyethyl-4-methylaniline.

In a particular embodiment of the present application, the raw materials can further include various additives that are applicable to oral conditions, including but not limited to at least one of fluorescer, indicator, viscosity modifier, wetting agent, antioxidant, stabilizer, and diluent.

Step (2) Mixing the weighed raw materials except reinforcing fiber, obtaining a composite resin monomer precursor.

During the specific implementation process, the raw materials except the reinforcing fiber can be dispersed and mixed homogeneously by mechanical stirring or ultrasonic oscillation.

Step (3) Impregnating the weighed reinforcing fiber into the composite resin monomer precursor for 1-5 hours, preferably 2-3 hours, at an impregnation negative pressure of less than or equal to 0.1 MPa, obtaining a composite resin monomer precursor-immersed reinforcing fiber.

In a particular embodiment of the present application, in order to increase the bonding strength between the reinforcing fiber and resin, the reinforcing fiber can be subjected to a pre-treatment before it is impregnated into the composite resin monomer precursor. The pre-treatment includes cleaning and surface modification.

Therein, the methods for the cleaning include but not limited to heat treatment method, solvent impregnation method or acid/base corrosion method. The heat treatment method means high temperature calcinating, for example 400° C. calcinating for 1 hour. The solvent impregnation method means impregnating with an organic solvent such as acetone for 5 hours. The acid/base corrosion method means impregnating with hydrochloric acid solution or sodium hydroxide solution at a certain concentration for a period of time, for example 0.5 hour. It should be noted that different methods for the cleaning could be used depending on the reinforcing fiber materials. For example, the acid/base corrosion method can be used for glass fiber, high temperature calcination process can be used for siliceous fiber, and the solvent impregnation method can be used for polymer fiber.

Further, the reinforcing fiber can be subjected to a surface modification after cleaning. The methods for the surface modification include but not limited to coupling agent modification, plasma surface modification or chemical grafting modification, or the like. All the listed methods for the surface modification belong to prior art, and the skilled person in the art can acquire the methods for performing the surface modification mentioned above, and will not be particularly limited herein in the present application. For example, the method recited in the document (Surface modification of carbon microspheres using a silane coupling agent, Sha Li, Feifei Duan, et al., Functional Material, 2011, No. 1, Vol 42, Pages 25-28) can be used to modify the surface of the reinforcing fiber through a coupling agent. This document is incorporated herein by reference in its entirety, and the contents thereof will not be repeated herein. The coupling agent used includes γ-methacryloxy propyl trimethoxysilane (KH-570), γ-mercaptopropyl triethoxysilane (KH-580), γ-aminopropyl trimethoxysilane (JH-A111), and the like.

Similarly, in a particular embodiment of the present application, the filler can be subjected to a surface modification before it is mixed with other raw materials. The methods for the surface modification include coupling agent modification, plasma surface modification treatment, or chemical grafting modification, or the like. The details can see the record of reinforcing fiber.

Step (4) Subjecting the composite resin monomer precursor-immersed reinforcing fiber to a solidification treatment, obtaining a dental composite resin material, wherein the solidification temperature is 100-200° C., preferably 120-160° C., the solidification time is 0.5-3 hours, preferably 1.5-2 hours, and the solidification pressure is 10-200 MPa, preferably 10-100 MPa, and more preferably 20-60 MPa.

The above solidification treatment under pressure and heating increases the contact area between ethylenically unsaturated monomer and initiator, and thus improving the efficiency of the solidification reaction, reducing polymer monomer residues, improving the biocompatibility of the composite resin material, and efficiently increasing the strength of the composite resin material.

It should be noted that the pressuring and heating equipment used in the present application are all commonly used in the art, as long as they can achieve the objects of the present application, and will not be particularly limited herein in the present application. For example, the pressuring and heating equipment from Shenzhen Chuangjiahong Machinery Co., Ltd can be used.

The technical solution of the present application will be described with reference to the specific examples below. The described examples are only a part of examples of the present application, but not all the examples. Based on the examples of the present application, any other example obtained by the ordinary skilled person in the art without inventive efforts falls within the protection scope of the present application.

EXAMPLE 1

Each of raw materials is weighed in according to the formulation of Example 1 in Table 1, then the weighed raw materials except glass fiber bundles are mechanically dispersed and mixed, obtaining a composite resin monomer precursor.

The weighed glass fiber bundles are calcinated at a temperature of 400° C. for 1 h; and after being cooled down to room temperature, they are subjected to a coupling agent modification treatment. Specifically, the glass fiber bundles can be impregnated into ethanol containing KH570 hydrolysate (wherein the volume ratio of KH570 hydrolysate to ethanol is 1:3), treated at 65° C. for 2 hours, and then dried at 100° C. for 4 hours.

The dried reinforcing fiber is impregnated into the composite resin monomer precursor for 2 hours, with the impregnation pressure of about negative 0.1 MPa, obtaining a composite resin monomer precursor-immersed reinforcing fiber. Then, the composite resin monomer precursor-immersed reinforcing fiber is subjected to a solidification treatment under the conditions of the solidification process in example 1 in Table 1, obtaining the dental composite resin material.

EXAMPLES 2-8

Raw materials and preparation process conditions recited in Table 1 are applied to prepare the dental composite resin material according to the method recited in Example 1. Therein, in Example 2, the fillers of lanthanum glass powder, nano-silicon oxide and nano-zirconium oxide are firstly subjected to a coupling agent modification before they are mixed with other raw materials. The treatment method is the same as that for the glass fiber bundles in Example 1. The dental composite resin material prepared in Example 6 has a A2 color of the VITA 16 colors shade guide, the dental composite resin material prepared in Example 7 has a A3 color of the VITA 16 colors shade guide, and the dental composite resin material prepared in Example 8 has a gingival color.

Measurement of Mechanical Performances

Flexural strength, flexural modulus, fracture toughness and light transmittance of the dental composite resin materials prepared in Examples 1-8 and obtained from commercial Trilor CAD/CAM fiber-reinforced block from Bioloren Sri are measured respectively, and the results are shown in Table 2.

Therein, the method for measuring the flexural strength is in accordance with YY/T 0710-2009/ISO 10477-2004, *"Dentistry Polymer-Based Crown and Bridge Materials"*. The method for measuring the flexural modulus is in accordance with ISO 10477: 2004 Ed. 2, *"Dentistry Polymer-Based Crown and Bridge Materials"*. The method for measuring the fracture toughness is in accordance with ISO 6872-2008, *"Dentistry—Ceramic Materials"*, and the method for measuring the light transmittance is in accordance with JC/T 2020-2010 *"Test Method for Transmittance of Translucent Fine Ceramics"*.

It can be seen from Table 2, that various performances of the dental composite resin materials prepared in the examples of the present application are excellent. The higher strength and toughness allow the material to maintain a good shape without crack or fracture when applied for dental restoration, whether during the processing, wearing, or application. Therefore, this material can be widely applied for dental restoration, and meet the demand of the market.

TABLE 1

The raw materials and preparation process conditions for preparing the dental composite resin materials of Examples 1-8.

| Raw materials and processing conditions | | Example 1 | Example 2 | Example 3 | Example 4 | Example 5 | Example 6 | Example 7 | Example 8 |
|---|---|---|---|---|---|---|---|---|---|
| Ethylenically unsaturated monomer | Bis-GMA | 1.9 | 6 | 5 | 3 | 8.75 | 5 | 5 | 5 |
| | UDMA | 7.6 | 8 | 12.5 | 12 | 19.25 | 12.5 | 12.5 | 12.5 |
| | Bis-EMA | 1.9 | — | — | 3 | — | — | — | — |
| | Epoxy resin E-44 | — | 2 | — | 3 | — | — | — | — |
| | TEGDMA | 3.8 | 4 | 7.5 | 6 | 7 | 7.5 | 7.5 | 7.5 |
| | HEMA | 3.8 | — | — | 3 | — | — | — | — |
| Reinforcing fiber | Glass fiber bundle | 56.7 | — | — | — | — | — | — | — |
| | Glass fiber fabric | — | 72 | — | — | — | — | — | — |
| | Quartz fiber fabric | — | — | 60 | 56 | — | 56.25 | 56.25 | 56.25 |
| | Quartz fiber block | — | — | — | — | 45.5 | — | — | — |
| Filler | Barium glass powder | 8.1 | — | 7.5 | 7 | 6.5 | 7.5 | 7.5 | 7.5 |
| | Lanthanum glass powder | — | 4 | 3.75 | — | 3.25 | 3.75 | 3.75 | 3.75 |
| | Silicon oxide-zirconium oxide composite powder | 8.1 | — | — | 3.5 | 3.25 | — | — | — |
| | nano-silicon oxide | 4.05 | 1.6 | 3.75 | — | 3.25 | 7.5 | 7.5 | 7.5 |
| | nano-zirconium oxide | 4.05 | 2.4 | — | 3.5 | 3.25 | — | — | — |
| Initiator | benzoyl peroxide | 0.0285 | 0.04 | 0.075 | 0.09 | 0.105 | 0.075 | 0.075 | 0.075 |
| Polymerization inhibitor | 2,6-di-t-butyl-p-cresol | 0.0475 | 0.06 | 0.05 | 0.06 | 0.105 | 0.05 | 0.05 | 0.05 |
| Accelerant | N,N-dihydroxyethyl paratoluidine | 0.019 | 0.06 | — | 0.03 | 0.07 | 0.05 | 0.05 | 0.05 |

TABLE 1-continued

The raw materials and preparation process conditions for preparing the dental composite resin materials of Examples 1-8.

| Raw materials and processing conditions | | Example 1 | Example 2 | Example 3 | Example 4 | Example 5 | Example 6 | Example 7 | Example 8 |
|---|---|---|---|---|---|---|---|---|---|
| Colorant | Iron oxide red | 0.007 | 0.021 | 0.042 | 0.032 | 0.021 | 0.004 | 0.006 | 0.048 |
| | Iron oxide yellow | 0.003 | — | — | 0.002 | 0.001 | 0.040 | 0.038 | 0.002 |
| | Iron oxide black | — | — | 0.001 | — | 0.002 | 0.001 | 0.001 | 0.005 |
| | Bismuth yellow | — | 0.009 | — | — | — | — | — | — |
| Ethylenically unsaturated monomer/(reinforcing fiber + filler) | | 19/81 | 20/80 | 25/75 | 30/70 | 35/65 | 25/75 | 25/75 | 25/75 |
| Fiber impregnation time (hour) | | 2 | 3 | 2.5 | 2 | 3 | 2.5 | 2.5 | 2.5 |
| Fiber impregnation pressure (MPa) | | ≤0.1 | ≤0.01 | ≤0.05 | ≤0.02 | ≤0.01 | ≤0.05 | ≤0.05 | ≤0.05 |
| Solidification temperature (° C.) | | 120 | 160 | 150 | 140 | 130 | 150 | 150 | 150 |
| Solidification pressure (MPa) | | 20 | 30 | 50 | 40 | 20 | 50 | 50 | 50 |
| Solidification time (hour) | | 1.5 | 1.5 | 2 | 2 | 1.5 | 2 | 2 | 2 |

Note:
the unit of numerical value for the raw material in Table 1 is part by weight, and per part by weight can be 100 g.

TABLE 2

Comparison between the performances of the dental composite resin materials prepared in Examples 1-8 and the product from Trilor.

| Example | Performance | | | |
|---|---|---|---|---|
| | Flexural strength/MPa | Bending modulus/GPa | Fracture toughness/ MPa · m$^{1/2}$ | Light transmittance/ % |
| Example 1 | 601 ± 19 | 18.25 ± 0.38 | 9.45 ± 0.16 | 41.56 |
| Example 2 | 634 ± 18 | 21.04 ± 0.99 | 13.77 ± 0.34 | 55.00 |
| Example 3 | 603 ± 15 | 17.65 ± 0.57 | 12.87 ± 0.45 | 47.37 |
| Example 4 | 617 ± 12 | 20.45 ± 0.86 | 13.60 ± 0.14 | 47.17 |
| Example 5 | 602 ± 12 | 19.28 ± 0.74 | 9.59 ± 0.36 | 42.48 |
| Example 6 | 608 ± 10 | 18.17 ± 0.65 | 12.59 ± 0.24 | 47.43 |
| Example 7 | 612 ± 15 | 19.36 ± 0.47 | 13.19 ± 0.16 | 48.11 |
| Example 8 | 605 ± 8 | 18.29 ± 0.56 | 12.89 ± 0.37 | 46.26 |
| Trilor | 541 ± 24 | 14.25 ± 0.86 | 7.65 ± 0.27 | 32.07 |

Measurement of Biocompatibility

With higher solidification degree, the composite resin material has less residual polymer monomer; then, the water absorption, solubility and chemical solubility of the materials are lower, and the biocompatibility of the materials is better. The water absorption, solubility and chemical solubility of the dental composite resin material prepared in Example 1 and commercial Trilor CAD/CAM fiber-reinforced block from Bioloren Srl are measured respectively, and the results are listed in Table 3. Therein, the method for measuring the water absorption and solubility is in accordance with YY/T 0710-2009/ISO 10477-2004, *"Dentistry Polymer-Based Crown and Bridge Materials"*, and the method for measuring chemical solubility is in accordance with ISO 6872-2008, *"Dentistry—Ceramic Material"*.

TABLE 3

Comparison between performances of example 1 and Trilor product

| Performance | Example 1 | Trilor |
|---|---|---|
| Water absorption/μg · mm$^{-3}$ | 14.8 | 36.45 |
| Solubility/μg · mm$^{-3}$ | 0.06 | 2.98 |
| Chemical solubility/μg · cm$^{-2}$ | 8.71 | 126.78 |

It can be seen from Table 3, that the dental composite resin material prepared in Example 1 has lower water absorption, solubility and chemical solubility compared to Trilor from Bioloren, indicating that the preparation method of the present application is beneficial for decreasing polymer monomer residues, thereby improving the biocompatibility and biosecurity of the dental composite resin material.

The method for preparing a dental composite resin material and articles prepared therefrom provided by the present application have been described in detail above. The theory and embodiments of the present application are illustrated with reference to specific examples herein. The above descriptions of the examples are only intended to be helpful to understand the method and main concept of the present application. It should be noted that, for those ordinary skilled person in the art, changes and modifications can be made to the present application without departing from the theory of the present application, and the changes and modifications fall within the protection scope of the claims appended by the present application.

The invention claimed is:

1. A method for preparing a dental composite resin material, comprising the steps of:
   (1) weighing each of raw materials, including an ethylenically unsaturated monomer, a reinforcing fiber, a filler, an initiator, an polymerization inhibitor and a colorant;
   wherein the ratio of the total weight of the reinforcing fiber and the filler to the weight of the ethylenically unsaturated monomer is 90:10-10:90; the initiator is 0.05-1% by weight relative to the weight of the ethylenically unsaturated monomer; the polymerization inhibitor is 0.05-1% by weight relative to the weight of the ethylenically unsaturated monomer; the colorant is 0.001-0.2% by weight relative to the total weight of the ethylenically unsaturated monomer, the reinforcing fiber and the filler; and the weight ratio of the filler to the reinforcing fiber is 10:90-55:45;
   (2) mixing the weighed raw materials except the reinforcing fiber, obtaining a composite resin monomer precursor;
   (3) impregnating the weighed reinforcing fiber into the composite resin monomer precursor for 1-5 hours, at an impregnation negative pressure of less than or equal to 0.1 MPa, obtaining a composite resin monomer precursor-immersed reinforcing fiber; and
   (4) subjecting the composite resin monomer precursor-immersed reinforcing fiber to a solidification treatment, obtaining the dental composite resin material, wherein the solidification temperature is 100-200° C., the solidification time is 0.5-3 hours, and the solidification pressure is 10-200 MPa.

2. The method according to claim 1, wherein the raw materials further include an accelerant, which is 0.05-1% by weight relative to the weight of the ethylenically unsaturated monomer.

3. The method according to claim 1, wherein the raw materials further include at least one of fluorescer, indicator, viscosity modifier, wetting agent, antioxidant, stabilizer, and diluent.

4. The method according to claim 1, wherein the ethylenically unsaturated monomer is selected from the group consisting of (methyl)acrylate, hydroxyl functionalized (methyl)acrylate, epoxy resin, and a combination thereof.

5. The method according to claim 1, wherein the reinforcing fiber is selected from the group consisting of carbon fiber, glass fiber, quartz fiber, siliceous fiber, ceramic fiber, polymer fiber, and a combination thereof; the reinforcing fiber is fiber bundle, fiber fabric or fiber block; the diameter of a single fiber of the reinforcing fiber is in the range of 0.1-25 μm; and the refractive index of the reinforcing fiber is in the range of 1.40-1.70.

6. The method according to claim 1, wherein the filler includes a type I filler and a type II filler; the type I filler is a filler with particle size in the range of 0.01-10 μm, and selected from the group consisting of inorganic fillers, pre-polymerized organic fillers that are insoluble in the composite resin monomer precursor, and a combination thereof; the refractive index of the type I filler is in the range of 1.48-1.60; the type II filler has a particle size in the range of 10-100 nm; and the weight ratio of the type I filler to the type II filler is 3:1-1:1.

7. The method according to claim 1, wherein the filler is subjected to surface modification before it is mixed with other raw materials, and the process of the surface modification includes coupling agent modification, plasma surface treatment modification or chemical grafting modification.

8. The method according to claim 1, wherein the colorant is selected from the group consisting of red colorant, yellow colorant, black colorant, and a combination thereof.

9. The method according to claim 1, wherein the initiator is selected from the group consisting of dicumyl peroxide, t-butyl peroxide, benzoyl peroxide, t-butyl peroxyacetate, t-butyl peroxybenzoate, and a combination thereof; and the polymerization inhibitor is 2,6-di-t-butyl-p-cresol.

10. The method according to claim 1, wherein the reinforcing fiber is subjected to a pre-treatment before impregnating; and the pre-treatment comprises cleaning and surface modification;
wherein, a method for the cleaning is a method selected from the group consisting of heat treatment, solvent impregnation, and acid/base corrosion; and a method for the surface modification is a method selected from the group consisting of coupling agent modification, plasma surface treatment modification, and chemical grafting modification.

11. A dental composite resin material prepared with the method according to claim 1.

12. The method according to claim 2, wherein the accelerant is N,N-dihydroxyethyl-4-methylaniline.

13. The method according to claim 1, wherein the ethylenically unsaturated monomer is selected from the group consisting of bisphenol A-glycidyl methacrylate, ethoxylated bisphenol A dimethacrylate, urethane dimethacrylate, triethylene-glycol dimethacrylate, hydroxyethyl methacrylate, poly(ethylene glycol) dimethacrylate, and bisphenol A epoxy resin, and a combination thereof.

14. The method according to claim 6, wherein the type I filler is selected from the group consisting of quartz, barium glass, lanthanum glass, borosilicate glass, silicon oxide-zirconium oxide composite powder, silicon oxide-ytterbium oxide composite powder, polycarbonate filled with or not filled with inorganic material, polyepoxide powder, and polymerized methacrylic resin.

15. The method according to claim 6, wherein the type II filler is selected from the group consisting of silicon oxide nanopowder and zirconium oxide nanopowder.

16. The method according to claim 8, wherein the red colorant is iron oxide red.

17. The method according to claim 8, wherein the yellow colorant is selected from the group consisting of iron oxide yellow, bismuth yellow, vanadium-zirconium yellow and cerium-praseodymium yellow, or a combination thereof.

18. The method according to claim 8, wherein the black colorant is iron oxide black.

* * * * *